(12) United States Patent
Erkkila et al.

(10) Patent No.: US 9,936,084 B2
(45) Date of Patent: Apr. 3, 2018

(54) WRIST COMPUTER WIRELESS COMMUNICATION AND EVENT DETECTION

(71) Applicant: POLAR ELECTRO OY, Kempele (FI)

(72) Inventors: Mika Erkkila, Oulu (FI); Niclas Granqvist, Magenwill (CH)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 15/158,881

(22) Filed: May 19, 2016

(65) Prior Publication Data
US 2016/0269572 A1 Sep. 15, 2016

Related U.S. Application Data

(62) Division of application No. 14/198,156, filed on Mar. 5, 2014, now Pat. No. 9,374,477.

(51) Int. Cl.
| | |
|---|---|
| *H04N 1/00* | (2006.01) |
| *A63B 24/00* | (2006.01) |
| *G06F 19/00* | (2018.01) |
| *G11B 27/30* | (2006.01) |
| *H04N 5/77* | (2006.01) |
| *H04N 7/18* | (2006.01) |
| *G11B 27/031* | (2006.01) |

(Continued)

(52) U.S. Cl.
CPC ......... *H04N 1/00204* (2013.01); *A63B 24/00* (2013.01); *A63B 24/0062* (2013.01); *G06F 1/163* (2013.01); *G06F 19/3481* (2013.01); *G11B 27/031* (2013.01); *G11B 27/30* (2013.01); *H04N 1/2129* (2013.01); *H04N 5/772* (2013.01); *H04N 7/185* (2013.01); *H04N 9/8045* (2013.01); *H04N 9/8205* (2013.01); *A61B 5/024* (2013.01); *A61B 5/1118* (2013.01); *A61B 5/1123* (2013.01); *A61B 2503/10* (2013.01); *H04N 2101/00* (2013.01); *H04N 2201/0096* (2013.01)

(58) Field of Classification Search
None
See application file for complete search history.

(56) References Cited

U.S. PATENT DOCUMENTS

| | | | |
|---|---|---|---|
| 8,140,143 | B2 | 3/2012 | Picard et al. |
| 2010/0331145 | A1 | 12/2010 | Lakovic et al. |

(Continued)

FOREIGN PATENT DOCUMENTS

| | | |
|---|---|---|
| CN | 102274028 A | 12/2011 |
| WO | 2012146273 A1 | 11/2012 |

OTHER PUBLICATIONS

Youtube video Feb. 6, 2014 Sony Smartwatch 2, https://www.youtube.com/watch?v=_dgmIVCvE3w.*

(Continued)

*Primary Examiner* — James Hannett
(74) *Attorney, Agent, or Firm* — Hoffmann & Baron, LLP

(57) ABSTRACT

A system includes a wrist computer and a portable video camera. The wrist computer acquires physical activity data measured by a sensor device, generates a time marker on the basis of the physical activity data, and transmits the time marker to the portable video camera according to a predefined wireless communication protocol. The portable video camera is configured to record video data, encode the video data into a video data file, and store the received time marker as meta data in the video file.

2 Claims, 7 Drawing Sheets

(51) Int. Cl.
*H04N 1/21* (2006.01)
*H04N 9/804* (2006.01)
*H04N 9/82* (2006.01)
*G06F 1/16* (2006.01)
*H04N 101/00* (2006.01)
*A61B 5/11* (2006.01)
*A61B 5/024* (2006.01)

(56) References Cited

U.S. PATENT DOCUMENTS

| | | |
|---|---|---|
| 2011/0263946 A1 | 10/2011 | el Kaliouby et al. |
| 2013/0330054 A1 | 12/2013 | Lokshin |
| 2014/0107493 A1* | 4/2014 | Yuen .................. H04W 4/027 600/473 |
| 2014/0156228 A1* | 6/2014 | Molettiere ............ G06F 19/322 702/189 |
| 2014/0233356 A1* | 8/2014 | Pattikonda ........... G04G 9/0064 368/13 |
| 2014/0249256 A1 | 11/2014 | Connor |
| 2014/0349256 A1* | 11/2014 | Connor ............... G09B 19/0092 434/127 |
| 2014/0364089 A1* | 12/2014 | Lienhart ................ H04W 4/12 455/412.2 |
| 2015/0135284 A1* | 5/2015 | Bogard ................. H04L 63/107 726/5 |

OTHER PUBLICATIONS

Extended European Search Report for corresponding European Application No. 15157314.4, pp. 1-3, dated Jul. 6, 2015.
European Search Report, Application No. 15 157 314.4, 5 pages, dated Feb. 23, 2016.

* cited by examiner

… (1) …

WRIST COMPUTER WIRELESS COMMUNICATION AND EVENT DETECTION

CROSS-REFERENCE TO RELATED APPLICATIONS

This application is a divisional of U.S. application Ser. No. 14/198,156, filed on Mar. 5, 2014, which is incorporated by reference herein in its entirety.

BACKGROUND

Field

The invention relates to a wrist computer configured to operate in connection with a camera system.

Description of the Related Art

There are available devices configured to measure physical activity of a user during physical activity. Such devices include motion sensors, heart rate sensors, etc.

SUMMARY

According to an aspect, there is provided a wrist computer comprising: a bi-directional wireless communication interface configured to communicate wirelessly with a portable video camera according to a predefined communication protocol; a processor configured to acquire physical activity data measured by a sensor device, to generate a time marker on the basis of the physical activity data, and to cause the bi-directional wireless interface to transmit the time marker to the portable video camera according to the predefined communication protocol.

According to another aspect, there is provided a portable video camera comprising: a camera device configured to capture video data; an encoder configured to encode the captured video data into a video data file; a bi-directional wireless communication interface configured to communicate wirelessly with a wrist computer according to a predefined communication protocol; and a processor configured to acquire a time marker from the wrist computer through the bi-directional wireless interface, and to store the acquired time marker as meta data in the video data file.

According to another aspect, there is provided a system comprising:

a wrist computer comprising a bi-directional wireless communication interface configured to communicate wirelessly with a portable video camera according to a predefined communication protocol; and a processor configured to acquire physical activity data measured by a sensor device, to generate a time marker on the basis of the physical activity data, and to cause the bi-directional wireless interface to transmit the time marker to the portable video camera according to the predefined communication protocol; and said portable video camera comprising: a camera device configured to capture video data; an encoder configured to encode the captured video data into a video data file; a bi-directional wireless communication interface configured to communicate wirelessly with the wrist computer according to the predefined communication protocol; and a processor configured to acquire a time marker from the wrist computer through the bi-directional wireless interface, and to store the acquired time marker as meta data in the video data file.

According to another aspect, there is provided a computer program product embodied on a non-transitory distribution medium readable by a computer and comprising program instructions which, when loaded into an apparatus, execute a computer process comprising: acquiring physical activity data measured by a sensor device; generating a time marker on the basis of the physical activity data; and causing a bi-directional wireless interface of the apparatus to transmit the time marker to a portable video camera according to a predefined communication protocol.

BRIEF DESCRIPTION OF THE DRAWINGS

In the following the invention will be described in greater detail by means of preferred embodiments with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
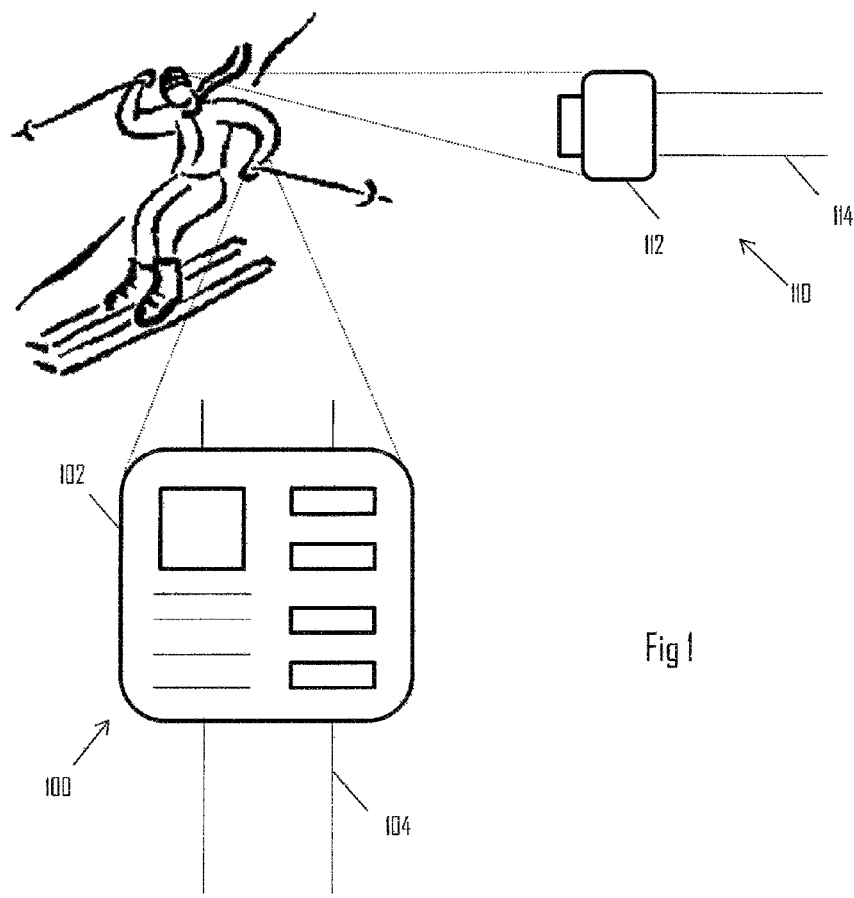
FIG. 1 illustrates an example of a scenario to which embodiments of the invention may be applied.

FIG. 1 illustrates a scenario to which embodiments of the invention may be applied and a system according to an embodiment of the invention. Referring to FIG. 1, a user carrying out a physical activity such as skiing, snowboarding, skateboarding, gymnastics, parkour, etc. may wish to record his/her performance by employing a camera system comprising one or more portable camera devices 110. The camera system may comprise a portable camera device 110 wearable by the user, e.g. attachable around the user's head (a head or helmet camera) and/or one or more cameras disposed in the environment in the area in which the user performs the physical activity. The wearable camera device 110 may comprise a casing 112 housing camera electronics and a strap 114 or another attachment mechanism attaching the camera device 114 to the user. The portable camera device may be configured to record and store video data.

The user may further wish to measure and monitor other characteristics of the physical activity by employing one or more sensor devices. Such sensor devices may include one or more motion sensors based on accelerometer, gyroscope, and/or magnetometer technology. The sensor devices may include sensors monitoring other characteristics such as cardiac activity or a location of the user. The cardiac activity may be measured by a heart rate sensor based on measuring electrocardiography of the user electrically through electrodes attached to the user's skin or optically from the user's wrist, for example. The location of the user may be determined by employing a positioning system such as a global navigation satellite system (GNSS).

The user may further employ a wrist computer 100 or another training computer 100 configured to communicate with the sensor device(s) and accumulate physical activity data measured by the sensor device(s). The training computer may be configured to communicate with the sensor device(s) external to the training computer over a bi-directional wireless communication connection, e.g. Bluetooth or Bluetooth Smart, Ant or Ant+, or another determined bi-directional wireless communication protocol. The training computer may be configured to communicate with the sensor device(s) comprised in the casing 102 of the training computer 100 via an internal hardwired connection. The training computer 100 may be configured to process the physical activity data provided by the sensor device(s) and, as a result of the processing, acquire performance metrics data representing characteristics of the physical activity as numerical values. Table 1 below provides a list of examples of the physical activity data and corresponding performance metrics data that may be processed from the physical activity data.

TABLE 1

| Physical Activity Data | Performance Metrics Data |
| --- | --- |
| GNSS data (location or speed) | Maximum speed |
| | Location relative to reference location |
| | Altitude relative to a reference altitude |
| | Speed above a threshold speed (horizontal, vertical) |
| Cardiac activity data | Heart rate |
| | Maximum Heart rate |
| | Heart rate relative to a reference (e.g. a heart rate zone) for a determined period of time |
| | Heart rate variability |
| | Energy expenditure in terms of burnt calories |

TABLE 1-continued

| Physical Activity Data | Performance Metrics Data |
| --- | --- |
| Motion activity data | Acceleration values |
| | Maximum acceleration |
| | Number of revolutions |

Referring to Table 1, the heart rate relative to a reference for a determined period of time may be considered as a time period spent observed to be spent in a determined heart rate zone defined by at least one heart rate threshold, e.g. the heart rate is below 140 beats per minute for one minute duration. Further examples of the performance metrics data that may be derived from the physical activity data may comprise heart rate samples, heart rate variation samples, heart beat interval samples, fat consumption rate, calorie consumption rate, consumed amount of calories, activity samples, speed and/or pace samples, power samples, cadence samples, altitude samples, temperature samples, location samples, distance elapsed, time elapsed, left-right balance, running index, training load, recovery time, galvanic skin response samples, fluid balance, skin temperature samples and/or heading samples.

The wrist computer 100 may comprise the casing housing the electronics of the wrist computer and an attachment mechanism such as a strap 104 attaching the wrist computer to the user's wrist.

Figure 2:
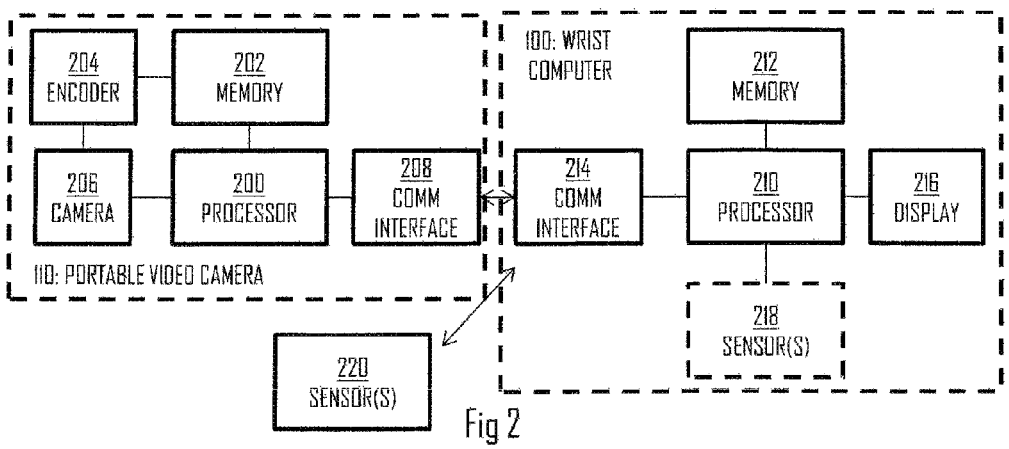
FIG. 2 illustrates a system according to an embodiment of the invention.

FIG. 2 illustrates a block diagram of a system according to an embodiment of the invention. The system may comprise at least one portable video camera 114 and the wrist computer 100. Additionally, the system may comprise further portable video cameras and/or one or more sensor devices 220 provided in a separate casing with respect to the wrist computer 100. Referring to the structure of the sensor device 220, the sensor device 220 may comprise a sensor configured to measure a physical characteristic such as motion or cardiac activity, a processor configured to process the measured physical characteristic into the physical activity data, and a wireless communication interface configured to transmit the physical activity data to the wrist computer.

The wrist computer 100 may comprise a bi-directional wireless communication interface 214 configured to establish bi-directional wireless communication connections with the portable video camera(s) 114 and, in some embodiments, unidirectional or bi-directional wireless communication connections with the sensor device(s) 220. The communication interface 214 may be configured to employ a predetermined wireless communication protocol, e.g. one of the protocols described above. The communication interface 214 may comprise wireless communication circuitries necessary for establishing the wireless connectivity, e.g. a radio frequency circuitry and a baseband circuitry. The wrist computer 100 may further comprise at least one processor 210 and at least one memory 212. The memory 212 may store a computer program code comprising program instructions configuring the processor 210 to execute embodiments of the invention in the wrist computer. The wrist computer 100 may further comprise a user interface comprising a display unit 216 configured to output graphical content to the user. The processor may control the operation of the display unit 216 and the graphical displayed by the display unit 216. In some embodiments, the wrist computer 100 comprises one or more sensors 218 connected to the processor 210 and configured to measure the physical activity data. The sensor(s) may comprise a motion sensor and/or a cardiac activity sensor.

The portable video camera 114 may comprise a bi-directional wireless communication interface 208 configured to establish a bi-directional wireless communication connection with the wrist computer 100. The communication interface 208 may be configured to employ a predetermined wireless communication protocol, e.g. one of the protocols described above. The communication interface 208 may comprise wireless communication circuitries necessary for establishing the wireless connectivity, e.g. a radio frequency circuitry and a baseband circuitry. The portable video camera may further comprise at least one processor 200 and at least one memory 202. The memory 202 may store a computer program code comprising program instructions configuring the processor 200 to execute embodiments of the invention in the portable video camera 110. The portable video camera may further comprise a camera device 206 configured to capture video data and an encoder 204 configured to encode the captured video data into a video data file. The camera device may comprise an image sensor implemented by a charge-coupled device (CCD) chip or a complementary metal-oxide semiconductor (CMOS) chip. The encoder 204 may encode the captured video data according to a determined motion picture encoding algorithm, e.g. moving picture experts group (MPEG) 2 or H.264. The encoded video data file may be stored in the memory 202.

The user employing the portable video camera 114 typically activates the video camera 114 to start recording the video data at the beginning of the physical activity and the video camera 114 captures and stores the video data for the duration of the activity. The duration may be several hours. The user may pause or stop the recording for some periods but typically the recorded video files store video data over several hours. When recording activity events having a short performance interval, e.g. jumps in snowboarding, the amount of useful video data is very small with respect to the total amount of video data. After all, the user is not interested in the video data recording the time interval the user spent in a ski lift, for example. Editing such video data is very tedious because the locations of the interesting events in the video data are difficult to find. On the other hand, it is inconvenient to constantly switch the camera 114 on an off and that is also prone to human oversights, e.g. forgetting to switch the camera 114 on.

Figure 3:
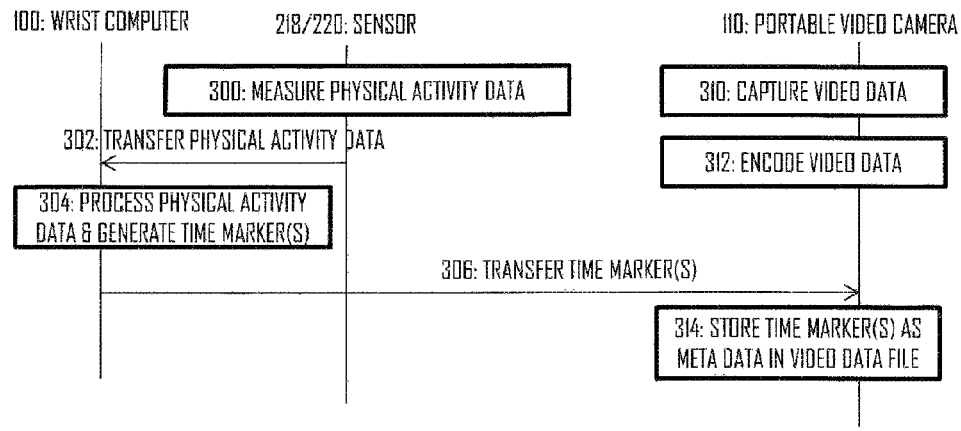
FIG. 3 illustrates a process for generating and transferring time markers between a wrist computer and a portable video camera according to an embodiment of the invention.

Let us now describe some embodiments of the invention with reference to using the physical activity in connection with the portable video cameras. FIG. 3 illustrates a signalling diagram of such an embodiment. Referring to FIG. 3, at least some of the sensor(s) 218, 220 is configured to measure the physical activity data during the physical activity (block 300). Meanwhile, the portable video camera 114 may capture the video data (block 310) with its camera device 206 and, in some embodiments, encode the video data (block 312).

The measured physical activity is transmitted by the sensor(s) and received by the wrist computer 100 in step 302. When the sensor is external to the casing of the wrist computer 100, the transfer in step 302 may be carried out over the wireless communication connection according to the determined wireless communication protocol. Upon acquiring the physical activity data in step 302, the processor 210 of the wrist computer 100 may be configured to generate a time marker on the basis of the physical activity data (block 304) and to cause the bi-directional wireless interface 214 to transmit (step 402) the time marker to the portable video camera 114 according to the predefined communication protocol employed in the wireless communication between the bi-directional wireless communication interfaces 214, 208. Upon acquiring the time marker from the wrist computer 100 through the bi-directional wireless communication interface 208 the processor 200 of the portable video camera 114 may be configured to store the acquired time marker as meta data in the video data file.

The time marker may indicate a determined time instant, time period, or time interval in the video data captured by the camera device.

The physical activity data may be used to detect interesting time instants or intervals in the video data. When the time markers are inserted into the video data file as the meta data, the indicated timings are visible in the editing phase which may facilitate the detection of the interesting events. This may increase the efficiency in editing the video data and provide the user with additional information on the physical activity.

In order to ensure that the time marker generated by the wrist computer 100 indicates the same timing as the time marker stored in the video data file by the portable video camera 110, the processors 200, 210 may be configured to synchronize their clocks by employing the wireless communication interfaces 208, 214. For example, several solutions for synchronizing clocks in a Bluetooth network have been disclosed in the art. In some embodiments, synchronization accuracy of one second or better is typically sufficient.

Figure 4:
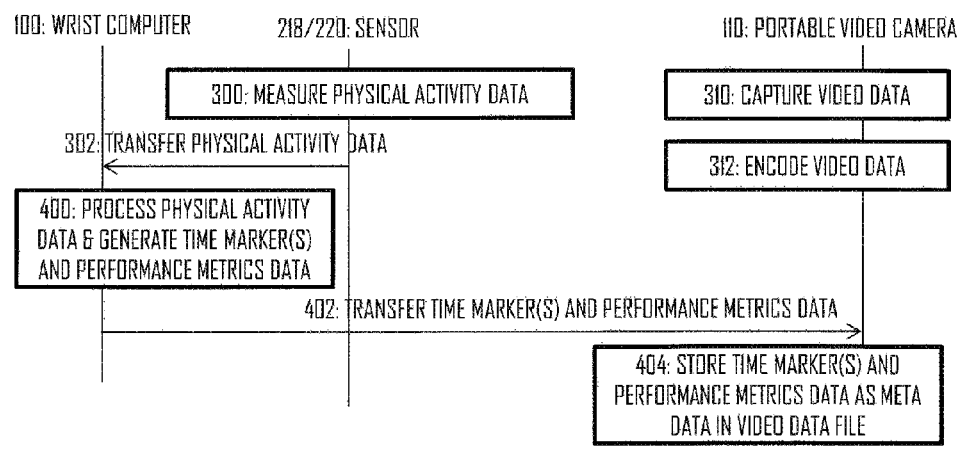
FIG. 4 illustrates a process for transferring other data together with the time marker according to an embodiment of the invention.

In an embodiment, the processor 210 is further configured to process the acquired physical activity data into said performance metrics data and to cause the bi-directional wireless communication interface 214 to communicate the performance metrics data to the portable video camera 114 according to the predefined communication protocol. FIG. 4 illustrates such an embodiment. In FIG. 4, the functions denoted by the same reference numbers as in FIG. 3 represent substantially similar functions. Referring to FIG. 4, upon receiving the physical activity data from the sensor(s) in step 302, the processor 210 may be configured to process the physical activity data into the performance metrics data and generate the time marker(s) on the basis of only the physical activity data or the performance metrics data or on the basis of them both (block 400). In step 402, the processor 210 configures the communication interface 214 to transmit the time marker(s) and at least some of the performance metrics data to the portable video camera 110. Upon receiving the time marker(s) and the performance metrics data through the communication interface 208, the processor 200 is configured to store the time marker(s) and the performance metrics data as the meta data in the video data file. This embodiment enables storing measured physical activity data represented by the performance metrics data in the video file. As a consequence, the user editing or viewing the video file may see his/her performance metrics such as the heart rate or speed at different time instants of the physical activity.

In an embodiment, the performance metrics data is associated with the time marker and stored as being associated to the time marker. As a consequence, the time marker binds the performance metrics data to a certain part of the video data in the video data file. As an example, the heart rate at a time instant of carrying out a jump may be stored in the video data file and viewed later on a computer, for example, after transferring the video data file from the portable video camera to the computer.

Figure 5:
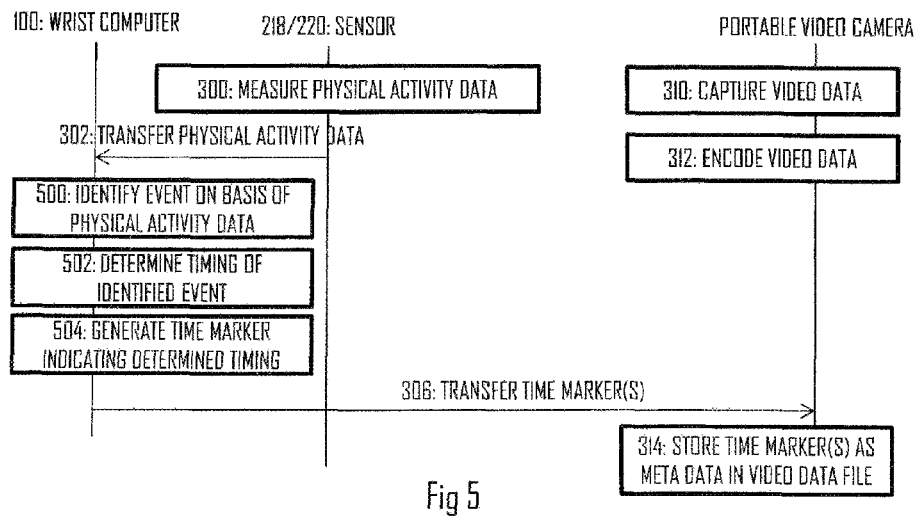
FIG. 5 illustrates a process for generating the time marker upon detecting an event according to an embodiment of the invention.

In an embodiment, the processor 210 is configured to identify a performance event from the physical activity data and to generate, in response to the identification of the performance event, the time marker indicating timing of the identified performance event. FIG. 5 illustrates an embodiment for detecting the performance event and generating a corresponding time marker. In FIG. 5, the functions denoted by the same reference numbers as in FIG. 3 represent substantially similar functions. Referring to FIG. 5, upon receiving the physical activity data from the sensor(s) in step 302, the processor 210 may be configured to identify the performance event from the physical activity data in block 500. Upon detecting the performance event, the processor 210 may be configured to check the timing of the performance event in block 502. In block 504, a time marker indicating the timing determined in block 502 is generated.

In an embodiment, block 502 may comprise checking the time at the instant of detecting the performance event from a clock of the wrist computer 100.

In another embodiment, block 502 may comprise further processing of the physical activity data and detecting the timing when the performance event had started, e.g. a timing that is prior to the timing of identifying the performance event. For example, the motion data representing a motion trajectory representing a performance event is processed by the processor upon receiving the motion data while the motion trajectory has already started. Accordingly, the identification of the performance event from the motion data may be made after the motion trajectory has started or even when it has ended in real time. The start of the performance event may be identified by processing the received motion data and determining, for example by comparing the motion data to a reference motion data representing a reference motion trajectory and stored in the memory 212, a motion data sample that is a first sample representing the identified performance event. A timing of the first sample may represent the start time of the performance event and the time marker may be generated to indicate the start time. A similar process may be used for physical activity data other than the motion data. Then, the time marker may be transferred to the portable video camera in step 306 and stored as the meta data in block 314. In an embodiment, an identifier of the identified performance event may be associated with the time marker and also transferred in block 206. The identifier may be a textual identifier or any other identifier. Accordingly, it gives a label to the time marker representing the performance event the time marker indicates.

Figure 6:
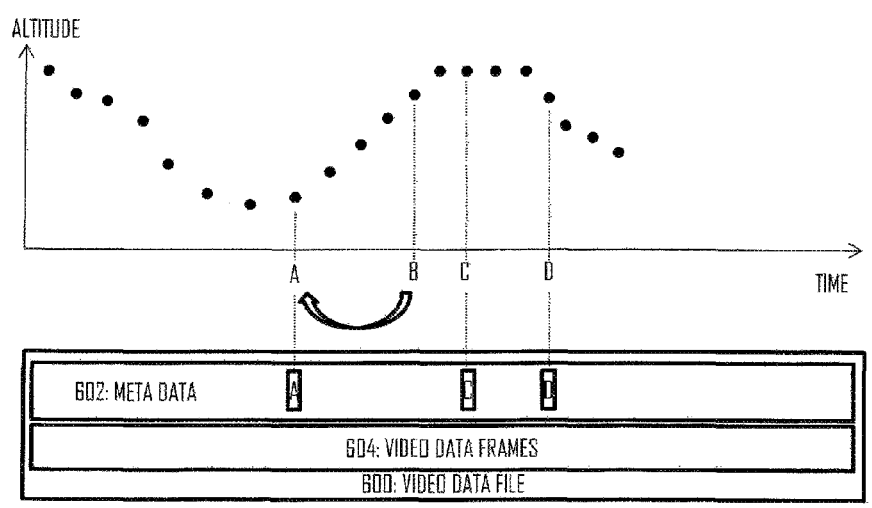
FIG. 6 illustrates generation and storing of the time markers according to an embodiment of the invention.

FIG. 6 illustrates some embodiments of FIG. 5 in the form of a graph representing measured altitude samples of the physical activity as a function of time. FIG. 6 also illustrates the video data file 600 comprising video data frames 604 as a function of the same time as the graph. The video data file may further store a start time and/or end time of the video recording of the video data frames such that the time markers may be mapped to the correct video data frames. The video data frames may be in the block 604 may be visualized such that the firstly recorded video frame is on the left edge of the video data frame block 604 and the last video frame is on the right edge of the video. This allows us to scale the timing of the video data frames to the time axis of the graph. Let us assume that the context where the system is used is alpine skiing. The first altitude samples until a sample denoted by A illustrate decreasing altitude which may be interpreted as the user skiing downhill. Thereafter, the altitude values start to increase relatively constantly, meaning probably that the user is in a ski lift. The processor 210 may be configured to search such a constant increase from the altitude values and, upon detecting that the altitude values have increased for a determined period of time defined by a threshold, e.g. at a time instant B, the processor 210 may be configured to determine that the performance event "ski lift" has been identified. Then, the processor 210 may be configured to trace back the altitude values and determine a first altitude sample that represents the performance event. In this case, it may be the first altitude sample in a series of constantly increasing altitude samples until timing B. This leads the processor to the sample represented by the time instant A and the processor may determine the timing of the time instant A and generate a time marker representing that timing. The processor 210 may further generate an identifier for the time marker, e.g. "ski lift starts" and transfer the time marker and the identifier to the portable video camera such that the time marker A may be stored in the meta data 602 of the video data file 600 to indicate one or more video data frames having the timing of the time marker A according to the clock of the portable video camera 110.

Generating the time marker indicating the time instant A may be considered to represent as an example of an embodiment where the processor is configured to record physical activity data for a performance period of a physical performance, wherein the performance period spans over at least a plurality of seconds, to apply post-processing to the recorded physical activity data after the performance period has ended, and to acquire the time marker as a result of said post-processing, wherein the time marker indicates a timing within the performance period. In the example of FIG. 6, the performance period may be a time interval between A and B or even a longer time interval. In a similar manner, the processor 210 may trace back any other event and arrange the time marker to indicate the start time of the detected performance event. Such an event may be a jump in which case the processor may trace back motion activity data to a sample indicating high impulse-type acceleration or sudden reduction of all acceleration values.

Further referring to FIG. 6, the first altitude sample representing end of the constant increase of the altitude is the sample having the time instant C. Upon detecting that the increase of the altitude has ended, e.g. detecting that at least a determined number of altitude samples demonstrate altitude increase below a determined altitude threshold, the processor 210 may determine that the user has exited from the ski lift and generate a corresponding marker. The time marker may represent the timing of the detection of the end of the increase or the processor may search the prior samples for the first sample representing the stop of the increase of the altitude. This time marker may then be assigned an identifier "end of ski lift", for example, and transferred to and stored in the meta data 602 to indicate one or more video frames having the timing of the time instant C according to the clock of the portable video camera 110.

Further referring to FIG. 6, upon detecting that the altitude values start to decrease (timing D), the processor 210 may generate the time marker representing a performance event "start of slope", and the time marker may indicate the timing of detecting the decrease. In this case, the processor may trigger the generation of the time marker upon detecting the first altitude sample that is lower than the previous altitude sample by a determined threshold, or upon detecting that the altitude has dropped over a determined threshold within a determined number of consecutive samples. This time marker may be generated to represent the time instant when the detection is made because typically the detection may be made within seconds of the start of the slope.

The identification may be made on the basis of motion activity data or cardiac activity data, for example. Table 2 below is an extension of Table 1 describing examples of performance events that may be identified on the basis of the physical activity data and/or the performance metrics data of Table 1.

TABLE 2

| Physical Activity Data | Performance Metrics Data | Performance Event |
|---|---|---|
| GNSS data (location or speed) | Maximum speed | Speeding |
| | Location relative to reference location | Location close to cameras |
| | Altitude relative to a reference altitude | high/low altitude location |
| | Speed above a threshold speed (horizontal, vertical) | Direction in the slope, ski lift |
| Cardiac activity data | Heart rate | |
| | Maximum Heart rate | Exciting/exhausting event |
| | Heart rate relative to a reference (e.g. a heart rate zone) for a determined period of time | Exciting/exhausting event |
| | Heart rate variability | Excitement/relaxation |
| | Energy expenditure in terms of burnt calories | Burnt calories limit achieved |
| Motion activity data | Acceleration values | jump, air time, big jump |
| | Maximum acceleration | hits, bumps, fall |
| | Number of revolutions | spin, flip, manoeuvre in the air |

It should be appreciated that any event detectable from the measured physical activity data may cause the generation of the time marker. One or more thresholds may be used in detecting the events. For example, speed or heart rate above a threshold may cause the generation of the time marker indicating a special event. The threshold and other parameters for detecting the events may be specified and stored in the memory 212 beforehand, e.g. through user inputs or factory-set values.

Figure 7:
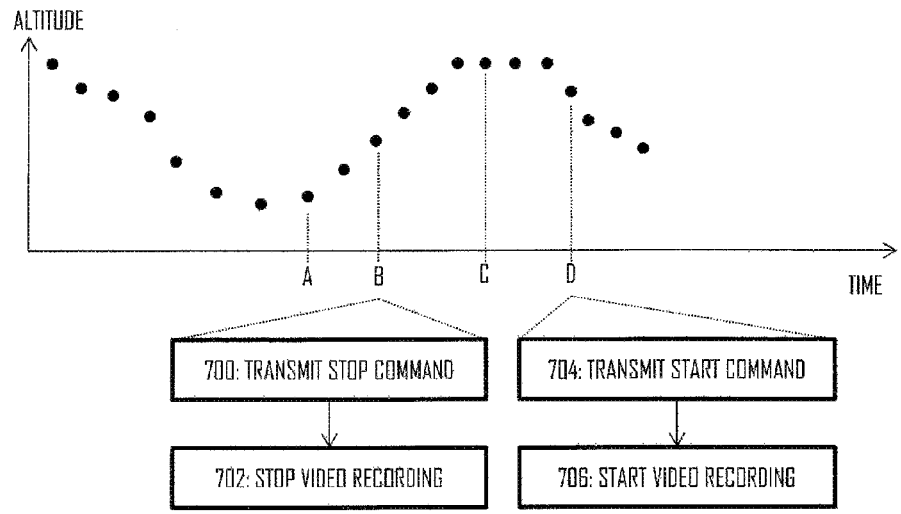
FIG. 7 illustrates a process for generating commands on the basis of the detected events according to an embodiment of the invention.

In an embodiment, the processor 210 is configured to generate, on the basis of the physical activity data, a start command triggering start of video recording and to cause the bi-directional wireless communication interface 214 to communicate the start command to at least one portable video camera 114 according to the predefined communication protocol. Referring to a graph of FIG. 7 similar to that of FIG. 6, the processor 210 may be configured to issue the start command or a stop command to the portable video camera in response to the detection of the performance event. The start command may cause the portable video camera to start video recording and the stop command may cause the portable video camera to stop video recording. Referring to the example of FIG. 7 in the context of the alpine skiing, upon detecting the constant increase in the altitude for a determined time interval, the processor 210 may identify the performance event "ski lift". The detection may cause the processor 210 to issue the stop command to the portable video camera 110. As a consequence, the processor 210 causes the communication interface 214 to transmit the stop command to the portable video camera 114 in block 700. Upon receiving the stop command through the communication interface 208, the processor 200 may be configured to cause the camera device 206 to stop recording of video data. Upon detecting the decrease in the altitude, the processor 210 may identify the performance event "start of slope". The detection may cause the processor 210 to issue the start command to the portable video camera 110. As a consequence, the processor 210 causes the communication interface 214 to transmit the start command to the portable video camera 114 in block 704. Upon receiving the start command through the communication interface 208, the processor 200 may be configured to cause the camera device 206 to start recording of video data. In this manner start or stop commands may be bound to other performance events and to other physical activity data as well.

Figure 8:
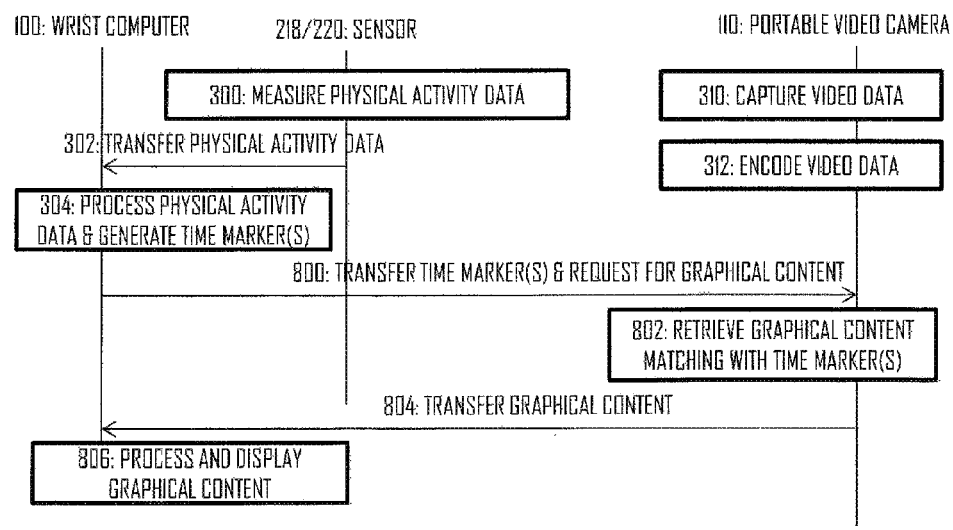
FIG. 8 illustrates a process for retrieving graphical content from the portable video camera according to an embodiment of the invention.

In an embodiment, the processor is configured to automatically retrieve graphical content associated with the time marker from the portable video camera within a predefined time period through the bi-directional wireless communication interface and, upon retrieving the graphical content, to cause the graphical interface to display the graphical content. FIG. 8 illustrates an embodiment of such a procedure. FIG. 8 is illustrated in the context of FIG. 3 but it may be realized in the context of FIG. 4 or 5, e.g. the identification of a determined performance event may cause the retrieval of the graphical content. The performance event may be, for example, a jump or a trick. As a consequence, the user may view the performance event from the graphical content displayed on the display unit of the wrist computer 100. Referring to FIG. 8, upon detecting on the basis of the physical activity data that the time marker is determined to be generated (block 304), the processor 210 may also determine that the detection triggers the retrieval of the graphical content from the portable video camera 110. As a consequence, the processor 210 may cause the communication interface 208 to transmit a request for the graphical content to the portable video camera 114 in step 800. The request may be comprised in the same message carrying the time marker(s) generated in block 304. Upon receiving the message in step 800, the processor 200 may process the request, retrieve graphical content indicated by the time marker, e.g. a video frame captured with the camera device 206, an image representing the video frame, or a set of video frames, and transfer the graphical content to the wrist computer 100 in step 804 through the communication interfaces 208, 214. Upon receiving the graphical content in step 804, the processor 210 processes the graphical content and causes the display unit to display the graphical content. The procedure of FIG. 8 may be automated so that the user needs not to instruct any commands to the wrist computer to trigger the retrieval of the graphical content.

In some embodiments, the communication interface 214 of the wrist computer may be connected to a plurality of portable video cameras. In such embodiments, the bi-directional wireless interface may be configured to communicate each or any time marker to a plurality of portable video cameras simultaneously or substantially simultaneously according to the predefined communication protocol. Similarly, the command or the request for the graphical content may be transmitted to the plurality of portable video cameras. Each portable video camera may operate, as the above-described manner. With reference to the embodiment of FIG. 8, the processor 210 may be configured to concatenate the graphical content received from the plurality of portable video cameras, e.g. create a play list from the graphical content, and then cause the display unit to display the graphical content according to the play list.

Figure 9:
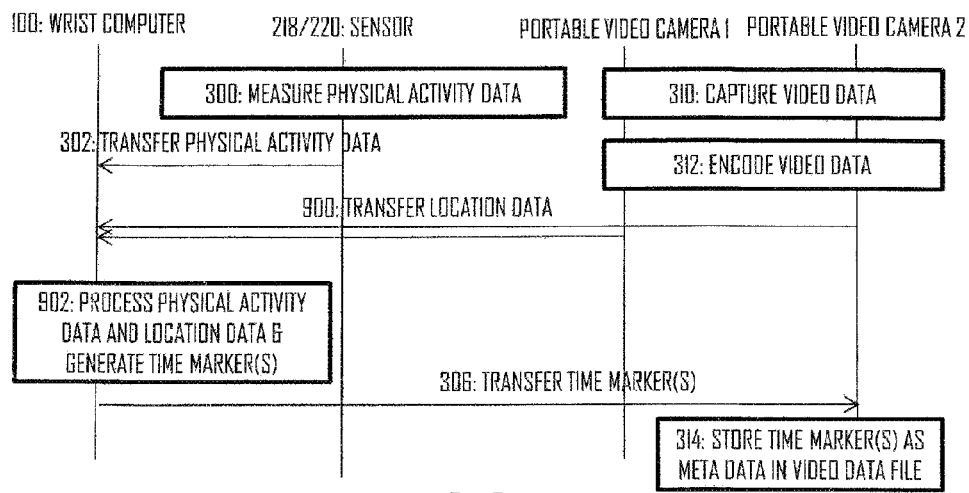
FIG. 9 illustrates a process for handling location data in connection with time markers according to an embodiment of the invention.

In an embodiment, the portable video camera 114 is provided with a positioning device, e.g. a GNSS receiver, configured to determine the location of the portable video camera. The processor 200 may be configured to determine the location of the portable video camera at determined time intervals and cause the communication interface 208 to transmit the location data to the wrist computer 110. The bi-directional wireless interface 214 of the wrist computer 100 may then be configured to receive the camera location data from at least one portable video camera according to the predefined communication protocol. The processor 210 may be configured to determine location of the wrist computer, e.g. by employing a GNSS receiver comprised in the wrist computer 100 or another positioning device, to compare the location of the wrist computer with the camera location data, and to generate the time marker when the comparison exceeds a predefined threshold. FIG. 9 illustrates a procedure according to this embodiment. In the embodiment of FIG. 9, the wrist computer 100 is connected to two portable video cameras 1 and 2 configured to capture and encode the video data (blocks 310, 312). The portable video cameras 1 and 2 are configured to transfer their location data to the wrist computer 100 in step 900 through respective communication interfaces by employing the determined communication protocol. Upon receiving the location data from the portable video cameras 1 and 2 in step 900, the processor 210 may compare the location of the wrist computer 100 with the locations of the portable video cameras 1 and 2. In an embodiment, the processor may select the portable video camera closest to the location of the wrist computer on the basis of the comparison. In such a case, the threshold mentioned above may represent the closest portable video camera. In this case, let us assume that the portable video camera 2 is selected to be closer to the wrist computer. As a consequence, the processor may choose to transmit the time marker(s) to the selected portable video camera 2 only and not to the other camera(s). Similarly, the command(s) or the request(s) for the graphical content may be transmitted to a selected subset of portable video cameras connected to the wrist computer 100, wherein the selection is made on the basis of the comparison of the location data.

In an embodiment, the wrist computer may send the start/stop commands to the portable video cameras according to the received location data. The wrist computer may employ the location data to command only the portable video camera closest to the wrist computer to record video data while keeping the other cameras recording function off. The other video cameras may still send the location data to enable the wrist computer to change the recording camera.

Figure 10:
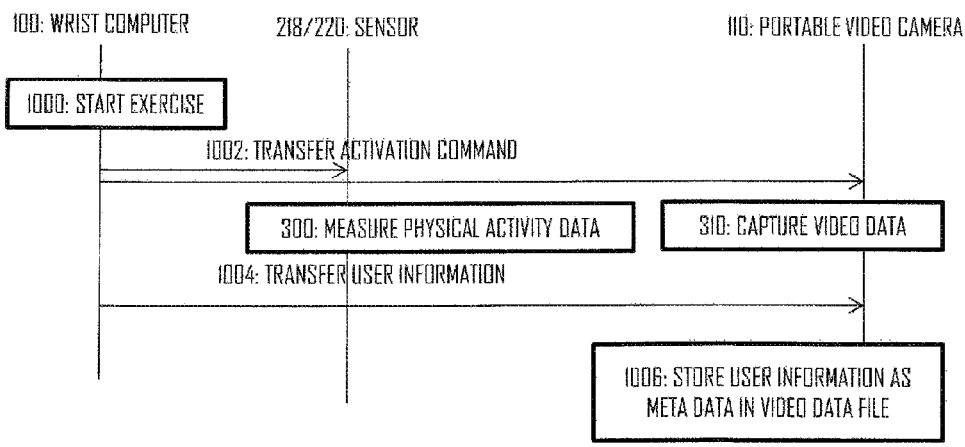
FIG. 10 illustrates a process for transferring user information to the portable video camera according to an embodiment of the invention.

In an embodiment, the processor 210 is configured to retrieve user information from the memory 212 and to cause the bi-directional wireless communication interface 214 to transmit the user information to the at least one portable video camera 114 according to the predefined communication protocol. The portable video camera may then store the user information as the meta data in the video data file. This enables identifying user(s) present in the video material comprised in the video data file in the editing phase, for example. FIG. 10 illustrates a procedure according to such an embodiment. Referring to FIG. 10, the wrist computer may trigger the start of the physical activity in block 1000 as a response to a user input, for example. As a consequence, the wrist computer may send a start command to the sensor(s) to start the measurements and/or to the portable video camera(s) 114 to start recording in step 1002. In some embodiments, step 1002 may be omitted and the user may activate the sensor(s) and the camera(s). At the start of the activity or during the activity, the wrist computer may acquire the user information from the memory and transfer the user information to the portable video camera in step 1004. Upon receiving the user information in step 1004, the portable video camera may store the user information as the meta data in the video data file in block 1006.

The user information may comprise any information enabling identification of the user of the wrist computer. The user information may comprise user credentials, user name, or a user identification code associated directly with the user. The user information may comprise user information indirectly associated with the user, e.g. an identifier of the wrist computer. Such an identifier may be a device address or a network address of the wrist computer 100. Such an address may be an internet protocol (IP) address or a medium access control (MAC) of the wrist computer 100.

Figures 11A, 11B:
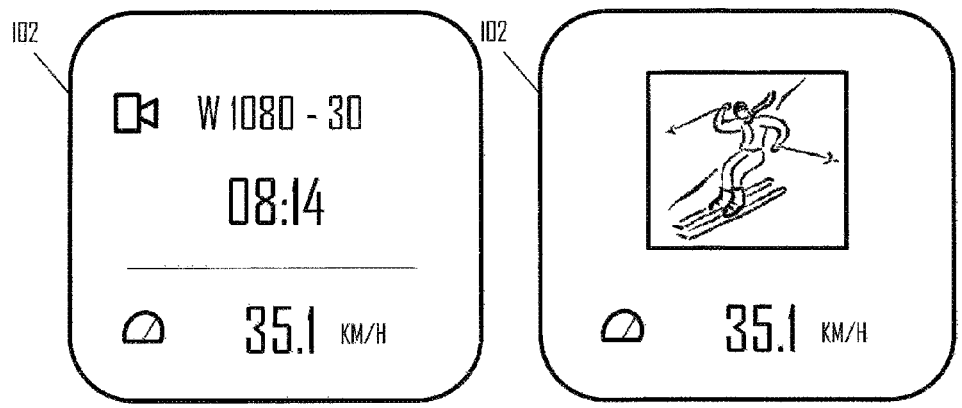
FIGS. 11A and 11B illustrate a combined display view comprising information on the video recording and performance metrics data according to some embodiments of the invention.

According to an aspect of the invention, the wrist computer 100 may be configured to display, in the same display view, the content retrieved from at least one portable video camera 114 together with the performance metrics data derived from the measurement data provided by the sensor(s). FIGS. 11A and 11B illustrate embodiments of the display view. Referring to FIG. 11A, the content retrieved from the portable video camera(s) may comprise camera information on the configuration or settings of the video recording or its progress. The camera information may comprise at least one of the following: a camera mode (video, photo, burst photo, time lapse), video resolution, frame rate, field of view, photo counter, video recording time, storage capacity in the memory 202, battery capacity of the camera, or notifications (low battery, too low temperature, memory low). The performance metrics data may include any one of those described in Tables 1 and 2, for example, e.g. heart rate, current heart rate zone, distance travelled, cadence, altitude, ascending, descending, total air time of previous jump, power, or power zone.

Referring to FIG. 11B, the content retrieved from the portable video camera(s) and displayed together with the performance metrics data may comprise one or more images of the recorded video, e.g. snapshots changing at determined intervals, e.g. one per second, or video streaming data. The video streaming data may be live view or a recorded view of a previous performance event.

Figure 12:
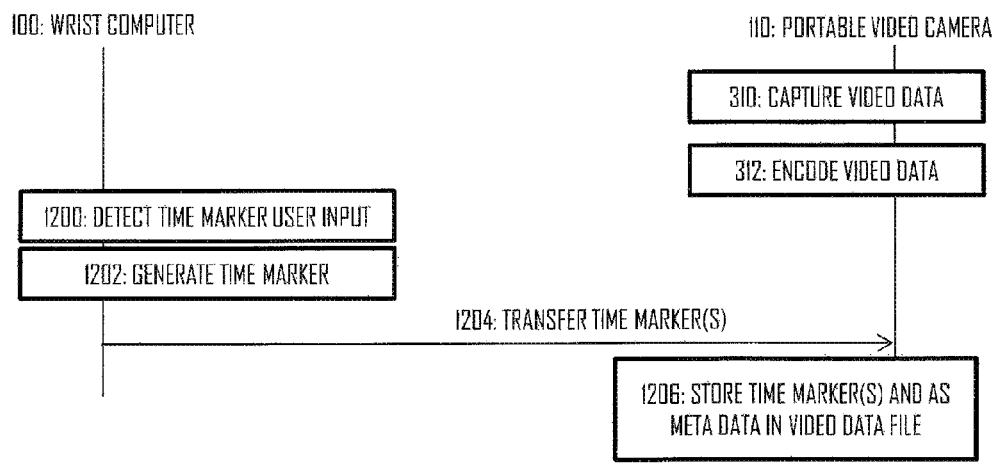
FIG. 12 illustrates a process for generating a user-initiated time marker according to an embodiment of the invention.

In an embodiment, the user interface of the wrist computer 100 comprises a time marker button or another time marker user input component that the user may use to trigger generation of the time marker indicating the time instant when the corresponding user input has been detected by the processor 210. FIG. 12 illustrates a procedure according to such an embodiment. Referring to FIG. 12, the processor 210 detects the user input requesting the generation of the time marker through the user interface of the wrist computer 100 (block 1200). In response, the processor may check the clock and generate the time marker indicating the current time instant (block 1202). The processor 210 may label the time marker as "user input", for example. In step 1204, the processor causes the communication interface 214 to transmit the time marker and the label to the portable video camera. Upon receiving the time marker and the label in step 1204 through the communication interface 208, the processor 200 of the portable video camera 114 may store the time marker in association with the label as the meta data in the video data file.

Figure 13:
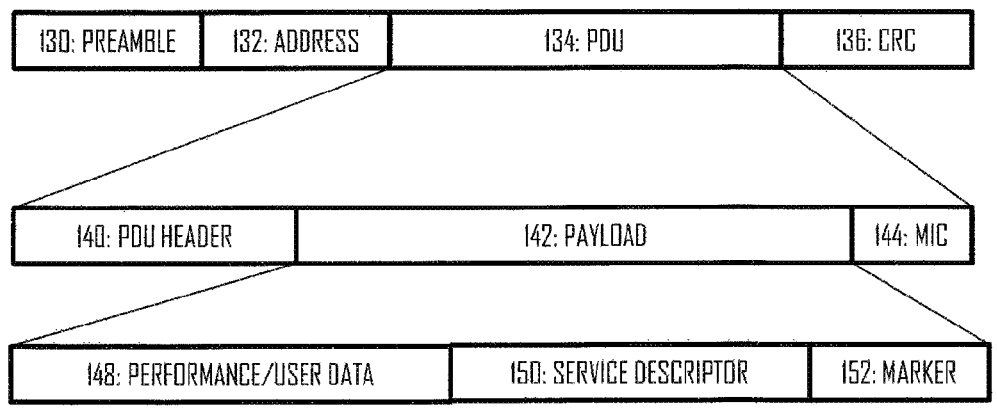
FIGS. 13 and 14 illustrate frame structures of data frames transmitted between the wrist computer and the portable video camera according to some embodiments of the invention.
Figure 14:
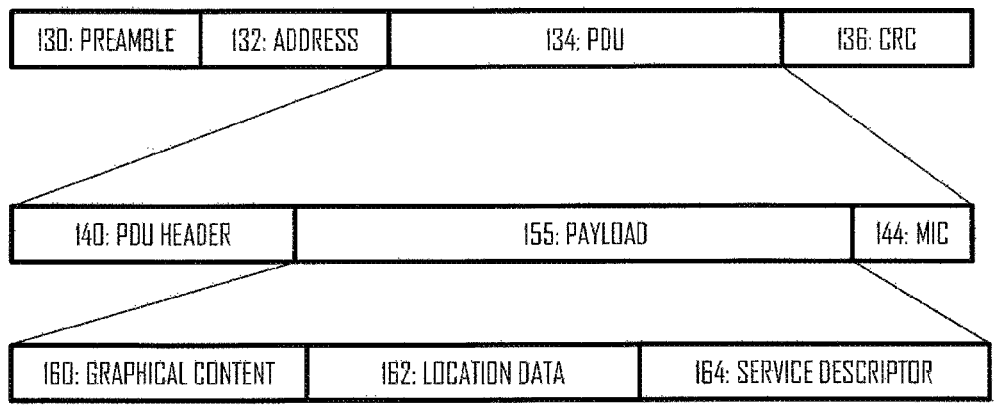

With respect to the wireless communication protocol employed between the wrist computer 100 and the portable video camera 110, let us now consider messages transferred between these apparatuses. FIG. 13 illustrates an example of a data frame transmitted from the wrist computer 100 to the portable video camera 110, and FIG. 14 illustrates an example of a data frame transmitted from the portable video camera 114 to the wrist computer 100. With reference to the embodiment of FIG. 13, the data frame is a data structure comprising fields 130, 132, 134, 136. Each field 130 to 136 comprises information bits, wherein some of the information bits may comprise control bits, e.g. signalling bits, while other information bits may comprise data bits, e.g. payload data bits.

In an embodiment, the data frame 600 is an advertising packet.

In an embodiment, the data frame 600 is a link layer data packet.

In an embodiment, a field 130 comprises a preamble including synchronizing bits. In an embodiment, the preamble is compliant with Bluetooth standard, such as Bluetooth 4.0 standard.

In an embodiment, a field 132 comprises access address data. The access address data field 132 may follow the preamble field 130, as shown in FIG. 13. The access address data may specify a physical link access code, e.g. a destination address of the data frame. In case of a broadcast transmission, the access address may be a broadcast address. In an embodiment, the access address data are compliant with Bluetooth standard, such as Bluetooth 4.0 standard.

In an embodiment, a field 134 comprises PDU (Protocol Data Unit) data. The PDU data comprises payload data. The payload data may include any payload data described above, e.g. the time markers, commands, or information transmitted from the wrist computer 100 to the portable video camera 110. The length of the payload data may vary from 0 to 27 octets, for example.

In an embodiment, the PDU data field 134 comprises PDU header data 140. The length of the PDU header may be 2 octets, for example.

In an embodiment, the PDU data field 134 comprises the actual payload data 142 comprising the above-described payload information, for example.

In an embodiment, the PDU data field 142 comprises message integrity check (MIC) bits 144. The length of the MIC may be 4 octets, for example.

In an embodiment, the PDU data field 134 is compliant with Bluetooth standard, such as Bluetooth 4.0 standard.

In an embodiment, a field 136 comprises Cycling Redundancy Check (CRC) bit or bits. In an embodiment, the CRC bits are compliant with Bluetooth standard, such as Bluetooth 4.0 standard.

In an embodiment, the payload data 142 comprise an information element 148 comprising performance metrics data or user information, as described above.

In an embodiment, the payload data 142 comprise an information element comprising service description data 150. The service description data 150 specifies the data type the wrist computer currently transmits, e.g. a command instructing the portable camera device. The command may be the above-described start/stop command, a request for retrieval of the graphical content, or a request for adding a time marker or information carried by the data frame into the video data file. Each command may have a unique bit combination in the service description data 150.

In an embodiment, the payload data 142 comprise an information element comprising the time marker 152. Each time marker may be transmitted in a separate data frame, or a plurality of time markers may be transmitted as aggregated to the same data frame. In case the time marker is associated with a label denoting the time marker, the label may be carried in the field 148.

Referring to FIG. 14, the data frame transmitted from the portable video camera 114 to the wrist computer 100 may comprise the fields 130 to 144 described above. The payload data field 155 may, however, carry different information.

In an embodiment, the payload data 155 comprise an information element comprising service description data 164. The service description data 164 specifies the data type the wrist computer currently transmits, e.g. a contents of the information transmitted to the wrist computer. The service description data 164 may indicate, for example, that the payload data 155 carries graphical content or location data. The payload data 155 may further comprise a field comprising the data indicated by the service, e.g. the graphical content 160 carrying the settings of the video recording and/or image frames, and location data 162 carrying the location data of the portable video camera.

In an embodiment, the payload data 142 and/or 155 may further comprise one or more field indicator bits indicating the presence/absence of certain fields in the payload data 142, 155. For example, a separate field indicator bit may be provided for each field 148 and 152 in the payload data 142 and for each field 160, 162 in the payload data 155. One value of the field indicator bit may indicate the presence of the corresponding field in the data frame and the other value of the field indicator bit may indicate the absence of the corresponding field in the data frame. The service description data 150, 164 may be present in all data frames and, in some embodiments, the field indicator bit may be comprised in the service description data 150, 164.

Instead of the wrist computer 100, the embodiments described above as executed by the wrist computer 100 may be carried out by another apparatus, e.g. a smart phone or a tablet computer.

Instead of, or in addition to, transmitting the time marker(s) to the portable video camera 110, the wrist computer 100 may transmit the time marker(s) to a determined service provided in a server computer, for example. The time marker(s) may be transmitted on real time over the wireless communication protocol or as a bundle after the physical activity, e.g. when the wrist computer is connected to a computer providing a connection to the server computer. The user may upload the time marker(s) to his/her user account in the server computer. Then, when using a video editing software the user may download the time marker(s) from the server computer and the video editing software may be configured to embed the time marker(s) into the video data automatically, e.g. by mapping the timings indicated by the time marker(s) to a time line of the video data frames. Accordingly, the computer executing the video editing software under the instructions from the user may be configured to open the video data file, retrieve the time marker(s) from the server computer, and embed the time marker(s) with the video data in the same display view displayed to the user. In this example, it may not even be necessary to store the time marker(s) as the meta data in the video data file because the association between the time marker(s) and the video data is made in the video editing phase.

The procedures described above in connection with FIGS. 3 to 14 and executed by the wrist computer 100 and the portable video camera 114 may also be carried out in the form of one or more computer processes defined by one or more computer programs, respectively. Separate computer processes may be executed in the wrist computer 100 and in the portable video camera 110. The computer program may be in source code form, object code form, or in some intermediate form, and it may be stored in some sort of carrier, which may be any entity or device capable of carrying the program. Such carriers include transitory and/or non-transitory computer media, e.g. a record medium, computer memory, read-only memory, electrical carrier signal, telecommunications signal, and software distribution package. Depending on the processing power needed, the computer program may be executed in a single electronic digital processing unit or it may be distributed amongst a number of processing units.

In an embodiment, there is provided a computer program product embodied on a transitory or non-transitory distribution medium readable by a computer and comprising program instructions which, when loaded into an apparatus, execute a computer process comprising: acquiring physical activity data measured by a sensor device; generating a time marker on the basis of the physical activity data; and causing a bi-directional wireless interface of the apparatus to transmit the time marker to a portable video camera according to a predefined communication protocol. The computer program product may be stored as a software package in a server computer, distributed to the wrist computer, a smart phone, or a similar smart device over the internet, and installed to the smart device after the user has bought the device. Before the installation of the computer program, the device may not be capable of executing embodiments of the invention but, after the installation, the device may be configured to operate according to any one of the above-described embodiments. The server computer may be understood as a network computer connected to the Internet to which client devices connect through the Internet. The client device, e.g. the smart device or a computer connected to the smart device, may send a request for retrieval of the software package to the server computer, and the server computer may send the software package as a response to the request.

As used in this application, the term 'processor' refers to all of the following: (a) hardware-only circuit implementations such as implementations in only analog and/or digital circuitry; (b) combinations of circuits and software and/or firmware, such as (as applicable): (i) a combination of processor(s) or processor cores; or (ii) portions of processor(s)/software including digital signal processor(s), software, and at least one memory that work together to cause an apparatus to perform specific functions; and (c) circuits, such as a microprocessor(s) or a portion of a microprocessor(s), that require software or firmware for operation, even if the software or firmware is not physically present.

This definition of 'processor' applies to all uses of this term in this application. As a further example, as used in this application, the term "processor" would also cover an implementation of a single processor, multiple processors, or a portion of a processor, e.g. one core of a multi-core processor, and its (or their) accompanying software and/or firmware. The term "processor" would also cover, for example and if applicable to the particular element, an application-specific integrated circuit (ASIC), and/or a field-programmable grid array (FPGA) circuit for the apparatus according to an embodiment of the invention.

The present invention is applicable to systems defined above. With respect to the communication protocols, the specifications of wireless communication protocols and their network elements develop rapidly. Such development may require extra changes to the described embodiments. Therefore, all words and expressions should be interpreted broadly and they are intended to illustrate, not to restrict, the embodiment. It will be obvious to a person skilled in the art that, as technology advances, the inventive concept can be implemented in various ways. The invention and its embodiments are not limited to the examples described above but may vary within the scope of the claims.

What is claimed is:

1. A portable video camera comprising:
   a camera device configured to capture video data;
   an encoder configured to encode the captured video data into a video data file;
   a bi-directional wireless communication interface configured to communicate wirelessly with a wrist computer according to a predefined communication protocol; and
   a processor configured to acquire a time marker from the wrist computer through the bi-directional wireless interface, the time marker indicating a determined time instant, time period, or time interval in the video data captured by the camera device, and to store the acquired time marker as meta data in the video data file, to acquire, from the wrist computer, performance metrics data associated with timing indicated by the time marker and representing a performance event performed by a user performing a physical activity, to store the performance metrics data as the meta data in the video data file, and further configured to receive, through the bi-directional wireless communication interface a request for transfer of graphical content indicated by the time marker, to retrieve graphical content from said time instant, time period, or time interval indicated by the time marker from the video data file, and to cause the bi-directional wireless communication interface to transmit the retrieved graphical content to the wrist computer for display.

2. A computer program product embodied on a non-transitory distribution medium readable by a computer and comprising program instructions which, when executed by an apparatus, perform a process comprising:
   acquiring video data from a camera device;
   encoding the captured video data into a video data file;
   acquiring a time marker from a wrist computer through a bi-directional wireless interface the time marker indicating a determined time instant, time period, or time interval in the video data captured by the camera device;
   storing the acquired time marker as meta data in the video data file;
   acquiring, from the wrist computer, performance metrics data associated with timing indicated by the time marker and representing a performance event performed by a user performing a physical activity,
   storing the performance metrics data as the meta data in the video data file;
   receiving, through the bi-directional wireless communication interface a request for transfer of graphical content indicated by the time marker;
   retrieving graphical content from said time instant, time period, or time interval indicated by the time marker from the video data file; and
   causing the bi-directional wireless communication interface to transmit the retrieved graphical content to the wrist computer for display.

* * * * *